United States Patent [19]

Pakchoian

[11] Patent Number: Plant 5,416

[45] Date of Patent: Mar. 12, 1985

[54] PLUM TREE, "MIDROSAS"

[75] Inventor: John D. Pakchoian, Fresno, Calif.

[73] Assignee: Pakchoian Farms, Fresno, Calif.

[21] Appl. No.: 542,446

[22] Filed: Oct. 17, 1983

[51] Int. Cl.[3] ..... A01H 5/03

[52] U.S. Cl. ..... Plt./38

[58] Field of Search ..... Plt./38

*Primary Examiner*—Robert E. Bagwill

*Attorney, Agent, or Firm*—Huebner & Worrel

[57] ABSTRACT

A plum tree characterized by its close similarity to the Late Santa Rosa (unpatented) plum tree but from which it is distinguished by ripening 5 or 6 weeks earlier and by the absence of the dark purple band along the ventral suture, which is characteristic of the Late Santa Rosa.

1 Drawing Figure

BACKGROUND OF THE NEW VARIETY

The present invention relates to a plum tree and more particularly to a new and distinct variety of plum tree known as the "Midrosas" which is broadly characterized by its general similarity to the Late Santa Rosa (unpatented) plum tree from which it is distinguished by ripening ten to fifteen days earlier, by its general similarity to the Early Santa Rosa (unpatented) plum tree from which it is distinguished by ripening from ten to twelve days later, the Early Santa Rosa sometimes being referred to as the "Regular Santa Rosa", and from which the new variety of plum tree is distinguished by the absence of the dark purple colored band along the ventral suture, which is characteristic of the Early and Late Santa Rosa Plum Trees.

The applicant is a tree fruit farmer who frequently examines his orchards hoping to find new mutations which produce fruit having improved size, flavor, appearance, storage or shipping characteristics, and/or which ripen at advantageous times as compared with the ripening periods of other varieties. The present variety was discovered by the applicant in his search for new varieties in June of 1979 as a single scaffold limb on a tree of the Late Santa Rosa variety in a commercial orchard of Late Santa Rosa Plum Trees located at Huntsman and Chestnut Aves. near the City of Fresno, Calif. The orchard was then approximately fifteen years old. It is believed that the subject variety was a mutation which produced the new variety. The Late Santa Rosa orchard in which the discovery was made was owned by Pakchoian Farms, A California Corporation, at the time of the discovery.

The mutuation was reproduced by the applicant's grafting of the new variety into the trees of a commercial orchard of plum trees at 5606 Clarkson Avenue, Selma, Calif., in January of 1981. The resultant progeny have been carefully observed. The resultant trees have borne fruit that show them to be true to the original mutuation in all observable aspects.

Commercially, the most significant attribute of the new variety is its earlier date of maturity in relation to the parent mutation and in its improved appearance in comparison with the Late Santa Rosa. Grown under substantially identical cultural practices, the new variety was harvested near Selma, Calif. on June 25, 1983, while the Late Santa Rose plum tree was harvested July, 7 and 8, 1983, each in a single picking. The new variety is usually from ten to fifteen days earlier than the Late Santa Rosa.

The most striking visual distinctions between the new variety and the Late Santa Rosa are the lack or absence of the dark colored band along the suture of the new variety in contrast to the presence of this characteristic dark purple coloration along the ventral suture of the Late Santa Rosa. The lack of the suture stripe results in an overall cleaner and more uniform coloration pattern.

The new variety produced fruit at full maturity by July 5, 1983 near Selma, Calif., the fruit being ready for harvest by June 25, 1983.

The color definitions used in this description are from Maerz and Paul *Dictionary of Color,* published in 1950.

BRIEF DESCRIPTION OF THE DRAWING

The drawing is a photograph in color of a characteristic twig with leaves, three whole plums of slightly different maturity, and a further plum halved at right angles to the suture plane to show internal coloration, all of the present variety of plum tree.

TREE

Size: Large. Controlled by pruning.

Vigor: Vigorous.

Figure: Upright to upright-spreading when young.Mature form and density determined by pruning.

Productivity: Regular bearer, productive.

Trunk:

- *Thickness.*—Medium.
- *Texture.*—Coarse.
- *Color.*—Gray-brown, (Plate 7-C-8) of old bark.
- *Lenticels.*—Numerous.

Branches:

- *Thickness.*—Medium.
- *Texture.*—Medium.
- *Color.*—Mature, one-year old shoots, Brown (Plate 13-F-9); young shoots Green (Plate 20-I-5), occasionally tinged red on exposed surfaces.

Leaves:

- *Shoot.*—Size — Medium to slightly above average; average length 13.8 cm.; average width 5.5 cm. Shape — Long obovate, tip accuminate. Color — Upper leaf surface Dark Green (Plate 24-L-5); lower leaf surface Light Green (Plate 23-E-5). Margin — Crenate, single near base of leaf, double and occasionally triple from mid-margin to leaf apex. Moderately deep serrations tipped with small brown gland. Petiole — Medium to moderately long in relation to leaf, length 18 to 22 mm.; average thickness 1.5 mm.; color Light Green (Plate 18-G-5). Glands — Usually two on base of leaf blade. Small in size, shape reinform. Light Green (Plate 18-J-7) when young. Stipules — Two at base of petiole, usually persistent. Greenish when young (Plate 18-J-7), darkening with age. Small size, 4 to 5 mm. long, 0.5 mm. wide.

Flowers:

*Dates of bloom.*—First bloom, Feb. 20, 1983; full bloom Mar. 1, 1983. Time of bloom average to slightly late in comparison with midseason blooming varieties.

*Size.*—Medium, overall diameter 12 to 14 mm.

*Color.*—White, (Plate 1-A-1).

*Amount.*—Medium, well distributed. Medium persistence. Usually two flowers per bud, four flowers per node.

*Bud scales.*—Surface glabrous. Color Dark Brown (Plate 8-J-10).

*Pedicel.*—Length 15 to 18 mm. Color Green (Plate 17-I-7).

*Petals.*—Size medium, shape broad ovate. Length 12 to 14 mm., width 10 to 12 mm. Margins undulate, often strongly cupped.

*Nectaries.*—Color Olive Green (Plate 13-J-3).

*Stamens.*—Length 8 to 9 mm., color white, average 25 in number, upright position.

*Anthers.*—Medium size. Color Yellow (Plate 10-J-3).

*Pistil.*—Length 9 to 10 mm., more or less equal to anthers. Color Light Green (Plate 17-H-4).

*Pollen.*—Moderate amount, about average for species.

FRUIT

Maturity: Described as fully mature fruit, nearly tree ripe maturity, July 5, 1983.

*Commercial maturity.*—First pick June 25, 1983; last pick July 1, 1983.

Size: Uniform, medium to large. Average axial diameter 47 mm. Average suture diameter 49 mm. Average cheek diameter 50 mm.

Form: Uniform. Nearly round in both lateral and axial aspects. Usually quite symmetrical.

Suture: A distinct narrow line extending from base to apex. Line usually blending well with coloration of surrounding surface. Suture at times superficially cross checked with very fine lines.

Ventral surface: Nearly round. Only very slightly lipped, usually on one side only, along apical shoulder. Symmetrical.

Stem cavity: Rounded, quite small, moderate deep 9 to 10 mm. Nearly circular in axial aspect, 10 to 12 mm. in diameter. Suture shows only on ventral side.

Base: Rounded to slightly truncate, at right angle to fruit axis.

Apex: Rounded with no tip.

Pistil point: Apical and slightly depressed.

Stem: Medium to slightly long. Average 19 to 23 mm. in length. Medium to slender in thickness, average 1.5 to 2 mm. Greenish-brown in color (Plate 14-J-6) darkening to full Brown with age (Plate 14-J-8).

Skin: Medium to slightly thick. Medium texture. Skin moderately acidic. Tenacious to flesh when soft ripe and then will partially peel free. No tendency to crack. Color Reddish-Purple (Plate 5-L-4), changing to full Purple with maturity (Plate 8-J-5). Color usually uniform. Pubescence lacking, moderate heavy bloom. Numerous dots and flecks more heavily around apex and apical shoulders. Base and basal shoulders have less flecking but have numerous coalesced surface lines circling the stem cavity.

Flesh:

*Color.*—Yellow (Plate 3-A-11) to Yellow-Red (Plate 3-J-11), often with red pigments bleeding into flesh from skin. Surface of pit cavity Yellow-Red (Plate 3-J-10).

*Texture.*—Moderately firm when full ripe.

*Juice.*—Abundant.

*Fibers.*—Numerous fine white fibers in flesh, tender.

*Ripening.*—Even.

*Flavor.*—Excellent, slightly acid.

*Aroma.*—Pronounced, distinct, very good.

*Eating Quality.*—Excellent.

Stone: Cling; adheres to flesh over most of stone surface. Numerous moderately long fibers over surface of stone.

*Size.*—Medium, 24 to 26 mm. long; 17 to 18 mm. wide; 9 to 10 mm. thick.

*Form.*—Somewhat irregular oval in lateral aspect with protruding wings near midpoint of ventral suture.

*Base.*—Oblique to stone axis, shorter on ventral suture side.

*Hilum.*—Small, narrow, somewhat eroded.

*Apex.*—Rounded with cuspidate to mucronate tip.

*Sides.*—Nearly equal.

*Ridges.*—Stone moderately smooth with only very low netted ridges over surface. In lateral aspect at least one deep groove 10 mm. long is present, more or less parallel to the ventral edge and 3 to 5 mm. back from the ventral edge. Basal shoulder moderately grooved for 7 to 8 mm. and converging basally.

*Pits.*—Few small pits present near or along ventral suture margin.

*Ventral edge.*—Narrow and usually winged from base to mid-suture. Apical shoulder irregular and somewhat eroded.

*Dorsal edge.*—Strong and deep groove from base to mid-suture. A less prominent groove often continues from above mid-stone to apex.

*Color.*—Buff (Plate 11-E-5).

*Tendency to split.*—None observed.

Use: Fresh market for both local and long distance shipping.

Keeping quality; Good.

Shipping quality: Good.

Resistance to insects and disease: No particular susceptibilities noted.

Although the new variety of plum tree possesses the described characteristics under the growing conditions prevailing in Fresno County, Calif., in the central portion of the San Joaquin Valley, it is to be understood that variations of the usual magnitude in characteristics incident to changes in growing conditions, fertilization, pruning and pest control are to be expected.

Having thus described and illustrated my new variety of plum tree, what is claimed as new and desired to be secured by Letters Patent is:

1. A new and distinct variety of plum tree substantially as illustrated and described which is characterized by its similarity to the Late Santa Rosa (unpatented), which it most nearly resembles and from which it is distinguished by bearing fruit which ripens 5 or 6 weeks earlier and by the absence of a dark-colored band along the suture, which is characteristic of the Late Santa Rosa.

* * * * *

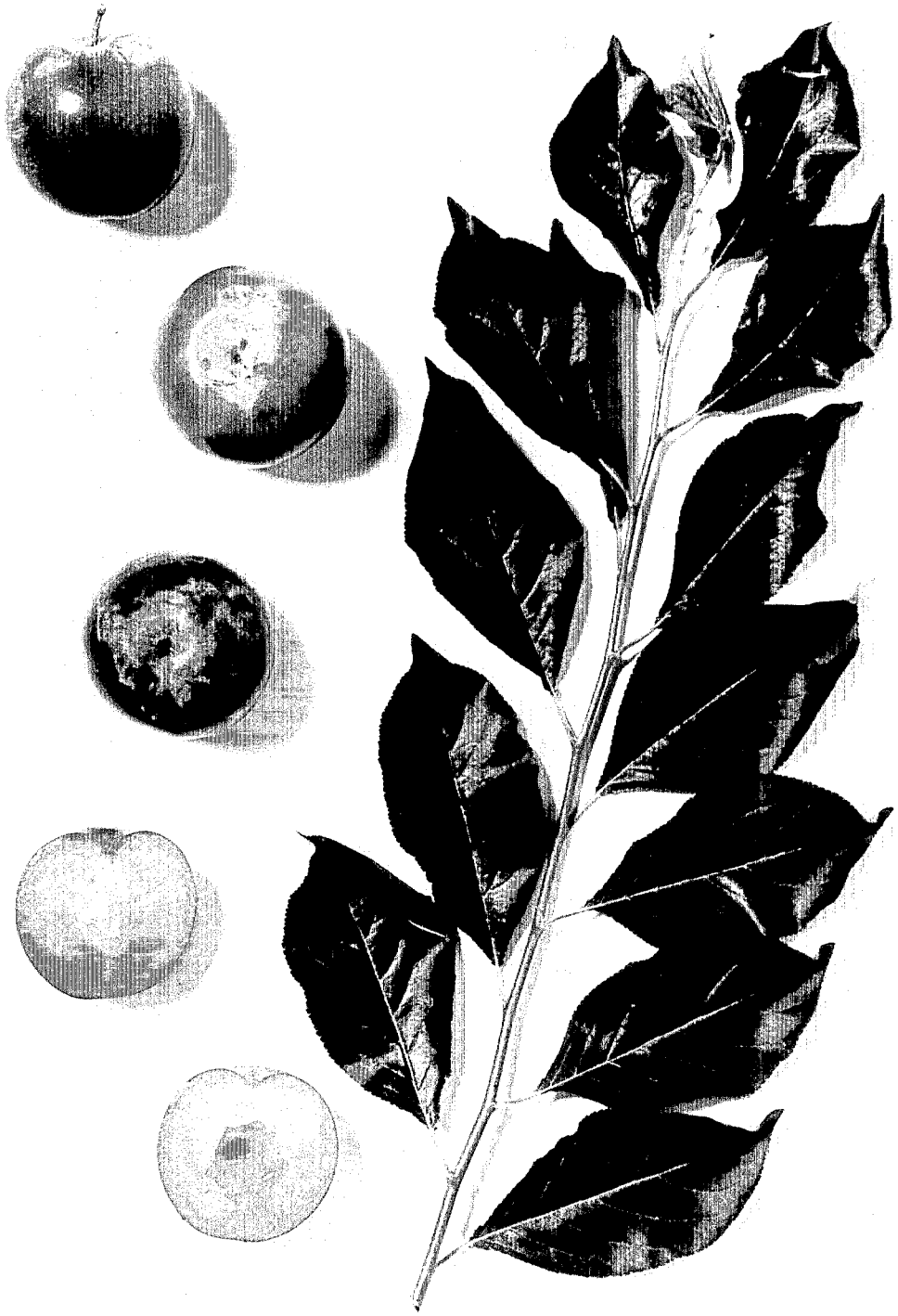

UNITED STATES PATENT AND TRADEMARK OFFICE

CERTIFICATE OF CORRECTION

PATENT NO. : PP 5,416

DATED : March 12, 1985

INVENTOR(S) : John D. Pakchoian

It is certified that error appears in the above–identified patent and that said Letters Patent are hereby corrected as shown below:

Column 1, line 49, delete "Late Santa Rose" and insert "Late Santa Rosa".

Signed and Sealed this

*Ninth* Day of *July 1985*

[SEAL]

*Attest:*

DONALD J. QUIGG

*Attesting Officer* *Acting Commissioner of Patents and Trademarks*